United States Patent [19]

Sleigh et al.

[11] Patent Number: 4,613,619

[45] Date of Patent: Sep. 23, 1986

[54] ANTI-ARRHYTHMIC AMINO-ALCOHOLS

[75] Inventors: Thomas Sleigh, Wishaw; David S. Savage, Glasgow; John K. Clark, Hamilton, all of Scotland

[73] Assignee: AKZO N.V., Arnhem, Netherlands

[21] Appl. No.: 704,491

[22] Filed: Feb. 22, 1985

[30] Foreign Application Priority Data

Feb. 28, 1984 [GB] United Kingdom ............... 8405112

[51] Int. Cl.⁴ ................. A61K 31/135; A61K 31/22; A61K 31/235; C07C 91/16; C07C 93/26; C07C 93/24

[52] U.S. Cl. .................... 514/546; 514/534; 514/549; 514/646; 514/821; 560/104; 560/107; 560/140; 560/221; 560/250; 560/252; 564/430; 564/442; 564/443; 260/501.1; 260/501.15; 260/501.18; 260/501.21

[58] Field of Search ........ 564/430, 443, 442; 560/140, 250, 252, 107, 104, 221, 194; 514/646, 549, 546, 534, 548; 260/456 A, 501.1, 501.15, 501.18, 501.21

[56] References Cited

U.S. PATENT DOCUMENTS

| | | | |
|---|---|---|---|
| 3,652,589 | 3/1972 | Flick et al. | 560/252 X |
| 3,974,157 | 8/1976 | Shetty et al. | 560/250 X |
| 4,391,827 | 7/1983 | Harbert et al. | 514/546 X |

FOREIGN PATENT DOCUMENTS 0048572  3/1982  European Pat. Off. ............ 514/546

Primary Examiner—Natalie Trousof
Assistant Examiner—Patricia M. Scott
Attorney, Agent, or Firm—Wegner & Bretschneider

[57] ABSTRACT

The invention concerns novel anti-arrhythmic amino-alcohol derivatives, characterized by the general formula (1)

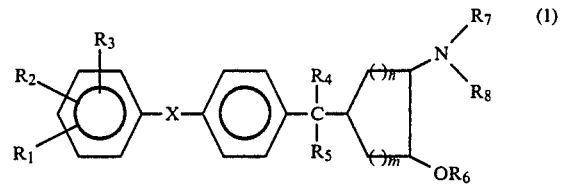

or pharmaceutically acceptable salts thereof, wherein $R_1$, $R_2$ and $R_3$ each independently represent hydrogen, alkyl having 1–6 carbon atoms, alkoxy having 1–6 carbon atoms, acyloxy having 1–6 carbon atoms, hydroxy, halogen or optionally alkyl-substituted amino;

$R_4$ represents hydrogen, hydroxy or alkyl having 1–6 carbon atoms, $R_5$ represents hydrogen or alkyl having 1–6 carbon atoms, $R_6$ represents hydrogen, acyl having 1–18 carbon atoms or alkyl having 1–6 carbon atoms, $R_7$ and $R_8$ each independently represent hydrogen or alkyl having 1–6 carbon atoms, X represents a direct bond or an oxygen atom, and n and m each independently are integers having a value of 1 or 2, whereby the sum of n and m is 2 or 3.

10 Claims, No Drawings

ANTI-ARRHYTHMIC AMINO-ALCOHOLS

The invention concerns novel anti-arrhythmic amino-alcohol derivatives, a process for the preparation of these compounds and pharmaceutical compositions containing these compounds.

The compounds according to the invention are characterized by the general formula (1)

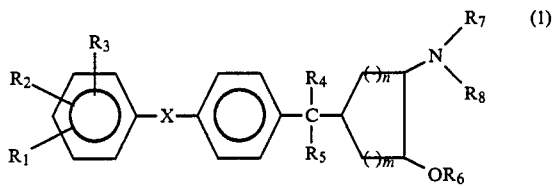

or pharmaceutically acceptable salts thereof, wherein $R_1$, $R_2$ and $R_3$ each independently represent hydrogen, alkyl having 1-6 carbon atoms, alkoxy having 1-6 carbon atoms, acyloxy having 1-6 carbon atoms, hydroxy, halogen or optionally alkyl-substituted amino;

$R_4$ represents hydrogen, hydroxy or alkyl having 1-6 carbon atoms, $R_5$ represents hydrogen or alkyl having 1-6 carbon atoms, $R_6$ represents hydrogen, acyl having 1-18 carbon atoms or alkyl having 1-6 carbon atoms, $R_7$ and $R_8$ each independently represent hydrogen or alkyl having 1-6 carbon atoms, X represents a direct bond or an oxygen atom, and n and m each independently are integers having a value of 1 or 2, whereby the sum of n and m is 2 or 3.

These compounds can be prepared by any method known in the art for the preparation of analogous compounds.

Advantageously as a starting compound for this preparation can be used the compound with the general formula (2):

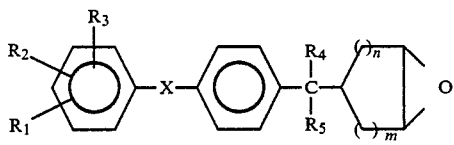

wherein $R_1$, $R_2$, $R_3$, $R_4$, $R_5$, X, m and n have the meanings defined above.

The compounds according to the invention are prepared by reacting the starting compound of formula 2 with a compound of the general formula (3)

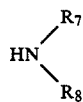

wherein $R_7$ and $R_8$ have the meanings defined above.

Compounds according to the invention wherein $R_7$ and $R_8$ both represent a hydrogen atom, can also be prepared by reacting the starting compound of formula (2) with an azide, preferably an alkali metal azide, such as sodium azide, followed by reduction of the resulting azide.

Optionally the above primary reactions may be followed by a chemical conversion from one compound into another compound of the invention. In this respect the hydroxy group in the definition of $R_1$, $R_2$ and $R_3$ as well as the alicyclic hydroxy group may be alkylated or acylated in the usual manner. This usual alkylation or acylation takes place in first instance at the phenolic hydroxyl group and in second instance at the alicyclic hydroxy group.

If a hydroxyl group is present that has to remain unsubstituted, it can preferably be protected by a well known hydroxyl protecting group, whereupon the alkylation or acylation is carried out, followed by a removal of the protecting groups.

A preferred and direct method for the preparation of compounds of formula 1, in which $R_6$ represents alkyl(-1-6 C) consists of the reaction of the epoxide according to formula (2) with an alcohol of 1-6 carbon atoms, such as methanol, ethanol, propanol, isopropanol, butanol, isobutanol, etc. Preferably this reaction is carried out in the presence of a Lewis acid, e.g. $BF_3$ etherate.

The alkoxy-ol compound thus obtained is subsequently oxidised to the corresponding alkoxyketone, thus converting the hydroxy group into a keto group.

The alkoxy-ketone thus obtained is finally converted into the corresponding alkoxy-amine of formula (1) by a reductive amination of the keto moiety in the usual manner.

Epoxide compounds according to the general formula (2) can be prepared according to methods known per se for analogous compounds. Favourably, these epoxides are prepared from the corresponding cycloalkene of the general formula (4) in the usual manner:

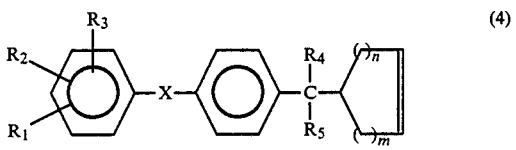

wherein $R_1$, $R_2$, $R_3$, $R_4$, $R_5$, m, n and X have the same meanings described before.

Methods for the preparation of the starting compounds of the general formula (4) are described in more detail in the examples of this specification.

Pharmaceutically acceptable salts of compounds according to the invention are in particular acid addition salts and quaternary ammonium salts. Acid addition salts can be obtained by reacting the free base according to formula (1) with acids, such as hydrochloric acid, sulphuric acid, phosphonic acid, acetic acid, propionic acid, methane sulfonic acid, fumaric acid, maleic acid, succinic acid, tartaric acid, lactic acid, citric acid, ascorbic acid, salicylic acid or benzoic acid. Ouaternary ammonium salts can be obtained by alkylating the free base according to formula (1), preferably using an alkylhalide such as methyl, ethyl, propylchloride or bromide. The acid addition salts are the preferred salts.

Depending upon the starting product and the method used the compounds of the invention may be obtained in the form of a specific diastereo isomer or a mixture of diastereo isomers. The mixture can be separated in the separate diastereo isomers in the usual manner using for example fractionated crystallization, column chromatography, etc. The separate diastereo isomer(s) may further be resolved into separate enantiomers in the usual manner, for example by using an optically active acid. These separate diastereo isomers and enantiomers also belong to the compounds according to the invention.

The compounds according to the invention are pharmaceutically active and in particular are antiarrhythmic agents.

The compounds can be administered either enterally or parenterally.

Mixed with suitable carriers they can be brought into a form suitable for oral administration such as pills, tablets and capsules. For injection purposes the compounds are dissolved, emulsified or suspended in a liquid suitable for injection. The compounds concerned can furthermore be administered in the form of a suppository or a spray.

The compounds according to the invention are preferably administered in a dosage of 0.01 up to 10 mg per kg body weight per day. For human use a dosage between 1.0 and 500 mg per day is recommended.

The alkyl group of 1 to 6 carbon atoms used in the definition of $R_1$, $R_2$, $R_3$, $R_4$, $R_5$, $R_6$, $R_7$ and $R_8$ is a hydrocarbon radical with up to 6 carbon atoms, such as methyl, ethyl, propyl, isopropyl, butyl, isobutyl, tert.butyl, pentyl and hexyl. More particularly, the alkyl group with 1-4 carbon atoms is the preferred alkyl group.

The alkyl group in the alkoxy radical as defined in $R_1$, $R_2$ and $R_3$ has the same meaning as explained above.

The acyloxy group in the definition of $R_1$-$R_3$ is preferably an alkanoyloxy group, in which the alkanoyl group is derived from an alkanoic acid with up to 6 carbon atoms, and more particularly with up to 4 carbon atom such as acetic acid, propionic acid and butyric acid.

The acyl group in the definition of $R_6$ is preferably derived from an aliphatic or araliphatic carboxylic acid with up to about 18 carbon atoms. More particularly those acyl radicals derived from an aliphatic carboxylic acid with 1-6 carbon atoms and especially 1-4 carbon atoms, such as acetic acid, propionic acid and butyric acid, and from a phenyl aliphatic carboxylic acid with 7-10 carbon atoms, such as phenylacetic acid, phenylpropionic acid and cinnamic acid are to be preferred.

By the optionally alkyl substituted amino radical in the definition of $R_1$-$R_3$ is meant an amino group in which one or two hydrogens may optionally be replaced by an alkyl (1-6 C) group.

More preferred compounds of formula I are those compounds in which—whether or not in combination—X represents a direct bond, $R_4$ and $R_5$ represent hydrogen, $R_6$ is hydrogen and n and m have both the value 1 or n is 1 and m is 2, as well as the acid addition salts thereof, in particular the methanesulphonate salt.

The preferred stereo isomer of formula I has the amino substituent to the alicyclic ring in β-position and at least the oxo substituent but preferably both other substituents to that ring in α-position.

In the following the invention is illustrated by examples which, however, by no way are intended to limit the scope of the invention. In these examples the compounds according to the invention are prepared from the corresponding epoxide-compounds. The preparation of these starting compounds is described below.

A.1.
[1,1'-Biphenyl]-4-yl(3-cyclopenten-1-yl)-methanone

A solution of bromine (11.9 ml) in methylene dichloride (50 ml) was added over 15 min. to a solution of 3-cyclopentene-1-carbonylchloride (30 g) in methylenedichloride (200 ml), maintained at −30° C. To this solution was added 1,1'-biphenyl (35.5 g) in a small volume of methylene dichloride.

The solution of acid chloride and 1,1'-biphenyl was added over 30 min. to a suspension of aluminium chloride (34 g) in methylene dichloride (100 ml), cooled to −50° C. The stirred mixture was allowed to warm up to room temperature over a period of 2 h., then it was poured into water. The methylene dichloride layer was washed three times with water and twice with brine, dried (MgSO$_4$) and the solvent was removed in vacuo. Crystallisation of the residue from methylene dichloride ether gave the dibromo intermediate (63.5 g). Chromatography of the mother liquor material on silica gel. followed by crystallisation from ether-light petroleum gave a further 7.5 g of [1,1'-biphenyl]-4-yl(3,4-dibromocyclopentyl)-methanone.

The dibromo intermediate (71 g) was dissolved in acetic acid (600 ml) and ether (600 ml) and the solution was cooled to 25° C. Zinc dust (150 g) was added over 20 min., while the temperature was reduced to 20° C. with external cooling, and the mixture was stirred at room temperature for 1.25 h. The zinc was filtered off on a dicalite pad and the filtrate was evaporated in vacuo. The residue was partitioned between methylene dichloride and water and the organic layer was washed with water three times, dilute caustic solution, water and finally brine. The solution was dried (MgSO$_4$) and the solvent was evaporated in vacuo. The product was crystallised from ethanol to give [1,1'-biphenyl]-4]-yl(3-cyclopenten-1-yl)-methanone (39 g) as a yellow solid, m.p. 92°-94° C.

The following compounds were obtained in a similar manner:

2. (4'-chloro-[1,1'-biphenyl]-4-yl)(3-cyclopenten-1 yl)-methanone, m.p. 103°-105° C.,
3. (3-cyclopenten-1-yl)(4'-methoxy-[1,1'-biphenyl-]4-yl)-methanone, m.p. 139°-140° C.,
4. (3-cyclopenten-1-yl)(4'-dimethylamino-[1,1'-biphenyl]-4-yl)-methanone, m.p. 172°-175° C.,
5. (3-cyclopenten-1-yl)(4-phenoxyphenyl)-methanone, m.p. 98°-100° C.

B. 1. 4-(3-Cyclopenten 1-ylmethyl)-1,1'-biphenyl

A mixture of [1,1'-biphenyl-]4-yl-(3-cyclopenten-1-yl)-methanone (32 g), hydrazine hydrate (40 ml) and potassium hydroxide (26 g) in diethylene glycol (500 ml) was heated under gentle reflux for 45 min. The low boiling materials were distilled off and the mixture was heated under reflux at 210°-220° C. for 1.25 h. The reaction mixture was cooled and poured into water, and the product was extracted with methylene dichloride. The organic layer was washed three times with water, dried and the solvent was removed in vacuo to give the crude product as a brown oil (30 g). Filtration of the product in toluene through silica resulted in a yellow oil (29 g), which solidified on standing. Crystallisation of a sample from light petroleum gave 4-(3-cyclopenten-1-ylmethyl)-1,1'-biphenyl as white plates, m.p. 47°-48° C.

The following compounds were prepared in a similar manner:

2. 4-Chloro-4'-(3-cyclopenten-1-ylmethyl)-1,1'-biphenyl, m.p. 59°-62 ° C.,
3. 4-(3-cyclopenten-1-ylmethyl)-4'-dimethylamino-1,1'-biphenyl. m.p. 79°-80° C.,
4. 1-(3-cyclopenten-1-ylmethyl)-4-phenoxy-benzene, obtained as an oil.

C. 1. 3-([1,1'-biphenyl]-4-ylmethyl)-6-oxabicyclo[3.1.0]hexane

Peracetic acid in acetic acid (60 ml; 40%) was added over 5 min. to a cooled mixture of sodium acetate (8g) and 4-(3-cyclopenten-1-ylmethyl)-1,1'-biphenyl (20 g) in chloroform (150 ml). The mixture was stirred vigorously at room temperature for 4 h., then it was cooled and a solution of sodium metabisulphite was slowly added. The chloroform layer was washed with water, dilute sodium hydroxide solution, water and brine, dried and evaporated to give a 1:3 mixture (TLC) of two products (20 g). Crystallisation from methylene dichloride-ether gave two crops, rich in the slower running isomer (TLC). Recrystallisation from methylene dichloride/ether gave pure (±)-(1α,3α,5α)-3-([1,1'-biphenyl]-4-ylmethyl)-6-oxabicyclo[3.1.0]hexane (9.6 g), m.p. 130°-132° C.

2. The resulting mother liquor material was separated into its two components by high pressure liquid chromatography, giving a further 2.6 g of slow running isomer and 5.3 g of crude fast running isomer. Recrystallisation of the latter from methylene dichloride-ether light petroleum gave (±)-(1α,3α,5α)-3-([1,1'-biphenyl]-4-ylmethyl)-6-oxabicyclo[3.1.0]hexene(4.1 g), m.p. 91°-94° C.

Alternative preparation

N-bromosuccinimide (27 g) was added over 25 min. to a suspension of 4-(3-cyclopenten-1-ylmethyl)-1,1'-biphenyl (27 g) in dimethylsulphoxide (320 ml) and water (40 ml). The solution was stirred at room temperature for 1.25 h., then it was poured into water and sodium metabisulphite solution was added. The resulting light brown precipitate was filtered off, dissolved in ethanol (300 ml) and the solution was heated under reflux with potassium hydroxide solution (30 ml, 10 N) for 15 min. The solution was poured into water to give a semi-solid mass, which was filtered off and dissolved in methylene dichloride. The solution was washed with water and brine, dried (MgSO$_4$) and the solvent was removed in vacuo. Crystallisation of the residue from ether-light petroleum gave (±)-(1α,3β,5α)-3-([1,1'-biphenyl]-4-ylmethyl)-6-oxabicyclo[3.1.0]-hexane (17 g). Chromatography of the mother liquor material gave a further 3.3 g of the same epoxide in a fairly pure form.

The following compounds were obtained in a similar manner by use of one of the above epoxidation methods:

3. (±)-(1α,3β,5α)-3-(4'-chloro-[1,1'-biphenyl]-4-ylmethyl)-6-oxabicyclo[3.1.0]-hexane, m.p. 89°-92° C.,
4. (±)-(1α,3α,5α)-3-(4'-chloro-[1,1'-biphenyl]-4-ylmethyl)-6-oxabicyclo[3.1.0]-hexane, m.p. 101°-102° C.,
5. (±)-(1α,3β,5α)-3-(4'-methoxy-[1,1,'-biphenyl]-4-ylmethyl)-6-oxabicyclo[3.1.0]-hexane,
6. (±)-(1α,3α,5α)-3-(4'-methoxy-[1 1'-biphenyl]-4-ylmethyl)-6-oxabicyclo[3.1.0]-hexane, m.p. 133°-134° C.,
7. (±)-(1α,3β,5α)-3-(4'-dimethylamino-[1,1'-biphenyl]-4-ylmethyl)-6-oxabicyclo-[3.1.0]-hexane, m.p. 115°-117° C.,
8. (±)-(1α,3α,5α)-3-(4'-dimethylamino-[1,1'-biphenyl]-4-ylmethyl)-6-oxabicyclo[3.1.0 -hexane, m.p. 120°-122 ° C.,
9. (±)-(1α,3β,5α)-3-(4-phenoxyphenylmethyl)-6-oxabicyclo[3.1.0]-hexane, m.p. 61°-62° C.,
10. (±)-(1α,3α,5α)-3-(4-phenoxyphenylmethyl)-6-oxabicyclo[3.1.0]-hexane, m.p. 60°-62° C.,
11. (±)-(1α,3β,5α)-3-(4'-hydroxy-[1,1'-biphenyl]-4-ylmethyl)-6-oxabicyclo[3.1.0]-hexane, m.p. 159°-167° C.,
12. (±)-(1α,3α,5α)-3-(4'-hydroxy-[1,1'-biphenyl]-4-ylmethyl)-6-oxabicyclo[3.1.0]-hexane, m.p. 154°-158° C.

D. 4-(3-cyclopenten-1-ylmethyl)-4'-hydroxy-1,1'-biphenyl

A mixture of (3-cyclopenten-1-yl)(4'-methoxy-[1,1'-biphenyl]-4-yl)-methanone (30 g), hydrazine hydrate (36 ml) and potassium hydroxide (36 g) in 2,2'-oxybisethanol (250 ml) was heated gently, at reflux temperature for 45 min. The low boiling material was distilled off and the mixture was heated under reflux, at 200° C. for 2 h. The cooled reaction mixture was poured into water, acidified with dilute hydrochloric acid and the resulting light brown precipitate was filtered off. This solid was dissolved in methylene dichloride. The solution was washed twice with water and dried (MgSO$_4$), and the solvent was removed. Trituration of the residue with light petroleum gave 4-(3-cyclopenten-1-ylmethyl)-4'-hydroxy-1,1'-biphenyl as a buff solid (25.5 g). A small sample, recrystallised from ether-light petroleum had m.p. 138°-140° C.

E. 4-(3-cyclopenten-1-ylmethyl)-4'-methoxy-1,1'-biphenyl

Zinc dust (40 g) was amalgamated with mercuric chloride (3 g) in a mixture of conc. hydrochloric acid (20 ml) and water (60 ml). The supernatant liquor was decanted off and the amalgam was washed briefly by decantation with fresh distilled water. Water (30 ml), conc. hydrochloric acid (45 ml), toluene (100 ml) and (3-cyclopenten-1-yl)-(4'-methoxy-[1,1'-biphenyl-]4-yl)-methanone (10 g) were then added and the mixture was heated under reflux for 2 h. The zinc was removed by filtration and the toluene layer of the filtrate was washed twice with water and once with brine. The solution was dried (MgSO$_4$) and the solvent was removed in vacuo to give 4-(3-cyclopenten-1-ylmethyl)-4'-methoxy-1,1'-biphenyl (9.1 g). A small sample, crystallised from ether-light petroleum had m.p. 75°-77° C.

F. (3-cyclopenten-1-yl)(4'-hydroxy-[1,1'-biphenyl]-4-yl) methanone

A solution of (3-cyclopenten-1-yl)(4'-methoxy-[1,1'-biphenyl]-4-yl)-methanone (42 g) in methylene dichloride (400 ml) was added over 1 h. to a solution of boron tribromide (30 ml) in methylene dichloride (200 ml) at −70° C. under an atmosphere of nitrogen. The reaction mixture was allowed to warm up slowly at room temperature and was stirred overnight. The solution was poured into water and the mixture was stirred for 10 min. The organic layer was washed twice with water, once with brine and dried (MgSO$_4$). Removal of the solvent gave (3-cyclopenten-1-yl) (4'-hydroxy-[1,1'-biphenyl]-4-yl)-methanone (38.5 g). A small sample recrystallised from ethanol had m.p. 153°-155° C.

G. 1. (±)-α-(3-cyclopenten-1-yl)-[1,1'-biphenyl]-4-methanol

Sodium borohydride (6 g) was added over 5 min. to a solution of [1,1'-biphenyl]-4-yl)(3-cyclopenten-1-yl)-methanone (25 g) in ethanol (250 ml) and tetrahydrofuran (200 ml). The reaction mixture was stirred at room temperature for 1.5 h., then it was poured into water and the resulting gummy solid was dissolved in methylene dichloride. The solution was washed with water three times, and with brine, dried (MgSO4) and the solvent was removed to give (±)-α-(3-cyclopenten-1-yl)-[1,1'-biphenyl]-4-methanol as an oil (22 g), which solidified on standing. A sample, recrystallised from ether-light petroleum had m.p. 7420 –75.5° C.

The following compounds were prepared in a similar manner:

2. (±)-α-(3-cyclopenten-1-yl)-(4'-methoxy-[1,1'-biphenyl])-4-methanol, m.p. 111°-112° C.,
3. (±)-α-(3-cyclopenten-1-yl)-(4'-hydroxy-[1,1'-biphenyl])-4-methanol, m.p. 161°-165° C.,
4. (±)-α-(3-cyclopenten-1-yl)-(4'-chloro-[1,1'-biphenyl])-4-methanol, m.p. 120°-121° C.,
5. (±)-α-(3-cyclopenten-1-yl)-4-phenoxy-benzenemethanol, obtained as a gum.

H.

1.(±)-([1,1'-biphenyl]-4-yl)-1-(3-cyclopenten-1-yl)-1-propanol

A solution of ([1,1'-biphenyl]-4 yl)(3-cyclopenten-1-yl)-methanone (17 g) in tetrahydrofuran (200 ml) was added over 25 min. to an ice-cooled solution of ethyl magnesium bromide, prepared in the usual way from magnesium (7 g) and ethylbromide (20.5 ml) in tetrahydrofuran (300 ml). After 10 min., the reaction mixture was carefully poured into water, acidified with dilute hydrochloric acid and extracted with ether. The ether layer was washed three times with water, dried (MgSO4), and the solvent was removed to give a brown oil (18.7 g). Filtration of the product, in toluene solution, through a silica column, followed by high pressure liquid chromatography, gave (±)-1-(1,1'-biphenyl-4-yl)-1-(3-cyclopenten-1-yl)-1-propanol (15 g), m.p. 82°-84° C.

The following compound was prepared in a similar manner:

2. (±)-1-(4'-chloro-1,1'-biphenyl-4-yl)-1-(3-cyclopenten-1-yl)-1-propanol, m.p. 85°-86° C.

K.

1.(±)-(1α,3β,5α)-α-(6-oxabicyclo[3.1.0]hex-3-yl)-[1,1'-biphenyl]-4-methanol and 2. (±)-(1α,3α,5α)-α-(6-oxabicyclo[3.1.0]hex-3-yl)-[1,1'-biphenyl]-4-methanol Peracetic acid in acetic acid (70 ml; 40%) was added with stirring, over 10 min., to an ice-cooled mixture of (±)-α-(3-cyclopenten-1-yl)-[1,1'-biphenyl-]4-methanol (22 g) in chloroform (250 ml) and sodium acetate (8 g). The reaction mixture was stirred vigorously at room temperature for 2 h., then it was cooled and sodium metabisulphite solution was added slowly. The organic layer was washed with water, dilute aqueous sodium hydroxide solution, with water twice, and finally with brine. The solution was dried and the solvent was removed to give a crude product (23 g), which was a 1:1 mixture of the two isomeric epoxides. Separation of the components by high pressure liquid chromatography gave (±)-(1α,3β,5α)-α-(6-oxabicyclo[3.1.0]hex-3-yl)-[1,1'-biphenyl]-4-methanol (10 g), m.p. 115°-128° C. (crystallised from methylene dichloride-ether) and (±)-(1α,3α,5α)-α-(6-oxabicyclo[3.1.0]hex-3-yl)-[1,1'-biphenyl]-4-methanol (12.5 g), m.p. 112°-123° C. (crystallised from ether-light petroleum).

The following compounds were obtained in a similar manner:

3. (±)-(1α,3β,5α)-4'-methoxy-α-(6-oxabicyclo[3.1.0-]hex-3-yl)-[1,1'-biphenyl]-4 methanol, m.p. 133°-134° C.,
4. (±)-(1α,3α,5α)-4'-methoxy-α-(6-oxabicyclo[3.1.0-]hex-3-yl)-[1,1'-biphenyl]-4-methanol, m.p. 135°-137° C.,
5. (±)-(1α,3β,5α)-4'-hydroxy-α-(6-oxabicyclo[3.1.0-]hex-3-yl)-[1,1'-biphenyl]-4-methanol, m.p. 174°-187° C.,
6. (±)-(1α,3β,5α)-4'-hydroxy-α-(6-oxabicyclo[3.1.0-]hex-3-yl- [1,1'-biphenyl]-4-methanol, m.p. 205°-210° C.,
7. (±)-(1α,3β,5α)-4'-chloro-α-(6-oxabicyclo[3.1.0]hex-3-yl)-[1,1'-biphenyl]-4-methanol, m.p. 114°-115° C.,
8. (±)-(1α,3α,5α)-4'-chloro-α-(6-oxabicyclo[3.1.0]hex-3 yl)-[1,1'-biphenyl]-4-methanol, m.p. 133°-135° C.,
9. (±)-(1α,3β,5α)-α-(6-oxabicyclo[3.1.0]hex-3-yl)-4-phenoxy-benzenemethanol, m.p. 71°-75° C.,
10. (±)-(1α,3α,5α)-α-(6-oxabicyclo[3.1.0]hex-3-yl)-4-phenoxy-benzenemethanol, m.p. 99°-100.5° C.,
11. (±)-(1α,3Δ,5α)-1-([1,1'-biphenyl]-4-yl)-1-(6-oxabicyclo-[3.1.0]hex-3-yl)-1-propanol, m.p. 126°-128° C.,
12. (±)-(1α,3α,5α)-1-([1,1'-biphenyl]-4-yl)-1-(6-oxabicyclo[3.1.0]hex-3-yl)-1-propanol, m.p. 125°-128° C.,
13. (±)-(1α,3β,5α)-1-(4'-chloro-[1,1'-biphenyl]-4 -yl)-1-(6-oxabicyclo[3.1.0]hex-3-yl)-1-propanol, m.p. 162°-164° C.,
14. (±)-(1α,3α,5α)-1-(4'-chloro-[1,1'-biphenyl]-4-yl)-1-(6-oxabicyclo[3.1.0]hex-3-yl)-1-propanol, m.p. 134°-137° C.

EXAMPLE I 1. (±)-(1α,2β,4α)-4-([1,1'-biphenyl]-4'-ylmethyl)-2-(2-methyl-2-propanamino)-cyclopentan-1-ol hydrochloride A mixture of (±)-(1α,3β,5α)-3-([1,1'-biphenyl]-4-ylmethyl)-6-oxabicyclo[3.1.0]-hexane (C.2.) (20 g), ethanol (130 ml), water (7 ml) and 2-methyl-2-propanamine (100 ml) was heated in an autoclave at 140° C. for 16 h. The solvent was removed in vacuo and the residue was dissolved in methylene dichloride. The solution was washed with water and brine, and dried (MgSO4). Hydrogen chloride gas was bubbled into the ice cooled methylene dichloride solution and the solvent was again removed in vacuo. Crystallisation from methylene dichloride-ether gave the crude hydrochloride, which was redissolved in ethanol. The ethanol solution was treated with charcoal and the product was crystallised three times from ethanol-ether to give (±)-(1α,2β,4α)-4-([1,1'-biphenyl]-4-ylmethyl)-2-(2-methyl-2-propanamino)-cyclopentan-1-ol hydrochloride (15.1 g) as a white solid, m.p. 189°-194° C. Melting point of the corresponding methanesulphonate salt: 180°-183° C.

EXAMPLE II

The following compounds were prepared in a similar manner as described in Example I from the corresponding (1α,3β,5α) oxabicyclo compounds and amines.

1. (±)-(1α,2β,4α)-4 -([1,1'-biphenyl]-4-ylmethyl)-2-methylamino cyclopentan-1-ol hydrochloride, m.p. 155°-160° C. (C.2.), 2. (±)-(-1α,2β,4α)-4-([1,1'-biphenyl]-4-ylmethyl)-2-butanamino-cyclopentan-1-ol hydrochloride, m.p. 203°-208° C. (C.2.), 3. (±)-(1α,2β,4α)-4-([1,1'-biphenyl]-4-ylmethyl)-2-(2-butanamino)-cyclopentan-1-ol hydrochloride, m.p. 168°-171° C. (C.2.), 4. (±)-(1α,2β,4α)-4-([1,1'-biphenyl]-4-ylmethyl)-2-methyl-1-propanamino)-cyclopentan-1-ol hydrochloride, m.p. 182°-185° C. (C.2.), 5. (±)-(1α,2β,4α)-4-(4'-chloro-[1,1'-biphenyl]-4-ylmethyl)-2-(2-methyl-2-propanamino)-cyclopentan-1-ol hydrochloride, m.p. 238°-253° C. (C.3.), 6. (±)-(1α,2β,4α)-4-(4'-methoxy-[1,1'-biphenyl]-4-ylmethyl)-2-(2-methyl-2-propanamino)-cyclopentan-1-ol hydrochloride, m.p. 208°-215° C. (C.5.), 7. (±)-(1α,2β,4α)-2-(2-methyl-2-propanamino)-4-(4-phenoxyphenylmethyl)-cyclopentan-1-ol hydrochloride, m.p. 201°-204° C. (C.9.), 8. (±)-(1α,2β,4α)-2-butanamino-4-(4-phenoxyphenylmethyl)-cyclopentan-1-ol hydrochloride, m.p. 158°-162° C. (C.9.), 9. (±)-(1α,2β,4α)-2-(2-butanamino)-4-(4-phenoxyphenylmethyl)-cyclopentan-1-ol hydrochloride, m.p. 162°-165° C. (C.9.), 10. (±)-(-1α,2β,4α)-4-(4'-hydroxy-[1,1'-biphenyl]-4-ylmethyl)-2-(2-methyl-2-propanamino-cyclopentan-1-ol (Z)-2-butenedioate (1:1) (salt), m.p. 123°-137° C. (C.11.).

11. (±)-(1α,2β,4α)-4-(3',4'-dimethoxy-[1,1'biphenyl]-4-ylmethyl)-2-(2-methyl-2-propanamino)-cyclopentan-1 ol methanesulphonate (salt), m.p. 192°-198° C.

12. (±)-(1α,2β,4α)-4-[4-(4-methoxyphenoxy)-phenylmethl]-2-(2-methyl-2-propanamino)-cyclopentan-1-ol hydrochloride, m.p. 152°-154° C.

13. (±)-(1α,2β,4α)-4-[4-(-3,4-dimethoxyphenoxy) phenylmethyl]-2-(2-methyl-2-propanamino)-cyclopentan-1-ol hydrochloride, m.p. 195°-201° C.

14. (±)-(1α,2β,4α)-2 (2-methyl-2-propanamino)-4-[4-(3,4,5-trimethoxyphenoxy)-phenylmethyl]-cyclopentan-1-ol hydrochloride, m.p. 189°-193° C.

15. (±)-(1α,2β,4α)-4-[4 (3,4-dichlorophenoxy)-phenylmethyl]-2-(2-methyl-2 propanamino)-cyclopentan-1-ol methanesulphonate (salt), m.p. 181°-190° C.

16. (±)-(1α,2β,4α)-4-[4-(4-methylphenoxy)-phenylmethyl]-2-(2-methyl-2-propanamino)-cyclopentan 1-ol hydrochloride, m.p. 177°-187° C.

17. (±)-(1α,2β,4α)-2-(2-methyl-2-propanamino)-4-[4-(3,4,5-trimethylphenoxy)-phenylmethyl]-cyclopentan-1-ol methanesulphonate (salt), m.p. 176°-179° C.

18. (±)-(1α,2β,4α)-2-(2-methyl-2-propanamino)-4-[4-(2,4,6-trimethylphenoxy)-phenylmethyl]-cyclopentan-1-ol methanesulphonate (salt), m.p. 155°-165° C.

EXAMPLE III

The following compounds were prepared from the corresponding (1α,3α,5α)-oxabicyclo compounds by use of the appropriate amine in a similar manner as described in Example I:

1. (±)-(1α,2β,4α)-4-([1,1'-biphenyl]-4-ylmethyl)-2-methylamino-cyclopentan-1-ol hydrochloride, m.p. 185°-196° C. (C.1.), 2. (±)-(1α,2β,4β)-4-([1,1'-biphenyl]-4-ylmethyl)-2-(2-methyl-2-propanamino)-cyclopentan-1-ol hydrochloride, m.p. 258°-263° C. (C.1.), 3. (±)-(-1α,2β,4β)-4-([1,1'-biphenyl]-4-ylmethyl)-2-(1-methylethylamino)-cyclopentan-1-ol hydrochloride, m.p. 234°-244° C. (C.1.), 4. (±)-(1α,2β,4β)-4-([1,1'-biphenyl]-4-ylmethyl)-2-dimethylamino-cyclopentan-1-ol hydrochloride, m.p. 204°-210° C. (C.1.), 5. (±)-(1α,2β,4β)-4-([1,1'-biphenyl]-4-ylmethyl)-2-diethylamino-cyclopentan-1-ol hydrochloride, m.p. 167°-173° C. (C.1.), 6. (±)-(-1α,2β,4β)-4-([1,1'-biphenyl]-4-ylmethyl)-2-butanamino-cyclopentan-1-ol hydrochloride, m.p. 204°-212° C. (C.1.), 7. (±)-(1α,2β,4β)-4-([1,1'-biphenyl]-4-ylmethyl)-2-(2-butanamino)-cyclopentan-1-ol hydrochloride, m.p. 215°-235° C. (C.1.), 8. (±)-(1α,2β,4β)-4-([1,1'-biphenyl]-4-ylmethyl)-2-(2-methyl-1-propanamino)-cyclopentan-1-ol hydrochloride, m.p. 219°-222° C. (C.1.), 9. (±)-(1α,2β,4β)-4-(4'-methoxy-[1,1'-biphenyl]-4-ylmethyl)-2-methylamino-cyclopentan-1-ol hydrochloride, m.p. 222°-233° C. (C.6.), 10. (±)-(1α,2β,4β)-4-(4'-methoxy-[1,1'-biphenyl]-4-ylmethyl)-2-(2-methyl-2-propanamino)-cyclopentan-1-ol hydrochloride, m.p. 273°-278° C. (C.6.), 11. (±)-(1α,2β,4β)-4-(4'-chloro-[1,1'-biphenyl]-4-ylmethyl)-2-(2-methyl-2-propanamino)-cyclopentan-1-ol hydrochloride, m.p. 248°-251° C. (C.3.), 12. (±)-(1α,2β,4β)-4-(4'-chloro-[1,1'-biphenyl]-4-ylmethyl)-2-methylamino-cyclopentan-1-ol hydrochloride, m.p. 201°-209° C. (C.3.), 13. (±)-(1α,2β,4β)-4-(4'-dimethylamino-[1,1'-biphenyl]-4-ylmethyl)-2-(2-methyl-2-propanamino)-cyclopentan-1-ol (E)-2-butenedioate (1:1) (salt), m.p. 256°-259° C. (C.8.), 14. (±)-(1α,2β, 4β)-2-(2-methyl-2-propanamino)-4-(4-phenoxyphenylmethyl)-cyclopentan-1-ol hydrochloride, m.p. 211°-216° C. (C.10.), 15. (±)-(1α,2β,4β)-2-(2-butanamino)-4-(4-phenoxyphenylmethyl)-cyclopentan-1-ol hydrochloride, m.p. 139°-141° C. (C.10.), 16. (±)-(1α,2β,4β)-4-(4'-hydroxy-[1,1'-biphenyl]-4-ylmethyl)-2-(2-methyl-2-propanamino)-cyclopentan-1-ol (Z)-2-butenedioate (1:1) (salt), m.p. Decomp. 183° C. (C.12.).

17. (±)-(1α,2β,4β)-4-[4-(4-methoxyphenoxy)-phenylmethyl]-2-(2-methyl-2-propanamino)-cyclopentan-1-ol hydrochloride, m.p 151°-155° C.

18. (±)-(1α,2β,4β)-2-(2-methyl-2 propanamino)-4-[4-(-3,4,5-trimethoxyphenoxy)-phenylmethyl]-cyclopentan-1 ol hydrochloride, m.p. 169°-171° C.

19. (±)-(1α,2β,4β)-4-[4 (3,4-dichlorophenoxy)-phenylmethyl]-2-(2-methyl-2-propanamino)-cyclopentan-1-ol methanesulphonate (salt), m.p. 105°-108° C.

20. (±)-(1α,2β,4β)-4-[4-(4-methylphenoxy)-phenylmethyl]-2-(2-methyl-2-propanamino)-cyclopentan-1-ol hydrochloride, m.p. 194°-208° C.

21. (±)-(1α,2β,4β)-2-(2-methyl 2-propanamino) 4-[4-(3,4,5-trimethylphenoxy)-phenylmethyl]-cyclopentan-1-ol methanesulphonate (salt), m.p. 153°-158° C.

22. (±)-(1α,2β,4β)-2-(2-methyl-2-propanamino)-4-[4 (2,4,6-trimethylphenoxy)-phenylmethyl]-cyclopentan 1 ol methanesulphonate (salt), m.p. 174°-176° C.

EXAMPLE IV (±)-(1α,2β,4β)-2-amino-4-([1,1'-biphenyl]-4-ylmethyl)-cyclopentan-1-ol Sodium azide (1.6 g), in the minimum amount of water for solution, was added to a solution of (1α,3α,5α)-3-([1,1'-biphenyl]-4-ylmethyl)-6-oxabicyclo[3.1.0-]hexane (C.1.) (4.5 g) in N,N-dimethyl-acetamide (45 ml) and the mixture was refluxed for 2 h. Water was added to the cooled reaction mixture and the product was extracted into ether. The ether extract was washed three times with water and once with brine, dried (MgSO₄) and the solvent was removed in vacuo to give a yellow oil (5.5 g) which was dissolved in ether and filtered through a silica column to remove polar material.

The resulting yellow oil (4.5 g) in tetrahydrofuran (60 ml) was added to a cooled suspension of lithium aluminium hydride (1.5 g) in tetrahydrofuran (50 ml). The mixture was heated gently under reflux for 45 min. then it was cooled and the excess of lithium aluminium hydride was destroyed by the careful addition of water, followed by a small amount of 4N sodium hydroxide solution. The inorganic material was filtered onto a dicalite pad and then re-suspended in a mixture of methylene dichloride and tetrahydrofuran; the process was repeated twice. After the removal of the solvent in vacuo, the resulting solid was dissolved in methylene dichloride. The solution was dried, the solvent was removed and the product was crystallised from etherlight petroleum to give the product as a white solid (3.45 g). The hydrochloride salt was prepared and re-crystallised twice from methanol-ethanol-ether to give (±)-(1α,2β,4β)-2-amino-4-([1,1'-biphenyl]-4-ylmethyl)-cyclopentan-1-ol hydrochloride (3.2 g), m.p. decomp. 203° C.

Example V

The following primary amino compounds were prepared in a similar manner as described in Ex. IV
1. (±)-(1α,2β,4β)-2-amino-4-(4'-methoxy-[1,1'-biphenyl]-4-ylmethyl)-cyclopentan-1-ol hydrochloride, m.p. 232°–240° C. (C.6.),
2. (±)-(1α,2β,4β)-2-amino-4-(4'-chloro-[1,1'-biphenyl]-4-ylmethyl)-cyclopentan-1-ol hydrochloride, m.p. decomp. 235° C. (C.4.),
3. (±)-(1α,2β,4β)-2-amino-4-([1,1'-biphenyl]-4-ylmethyl)-cyclopentan-1-ol hydrochloride, m.p. decomp. 220° C. (C.2.).

EXAMPLE VI

The following ester derivatives of 4-(4'-hydroxy-[1,1'-biphenyl]-4-ylmethyl)-2-(2-methyl-2-propanamino)-cyclopentan-1-ols were prepared by standard procedures: viz. reaction with acetic anhydride in pyridine in the case of the acetate derivatives and reaction with acid chloride in acetone/potassium carbonate in the case of the propionate and pivalate derivatives:
1. (±)-(1α,2β,4β)-4-(4'- acetyloxy -[1,1'-biphenyl]-4-ylmethyl)-2-(2-methyl-2-propanamino)-cyclopentan-1-ol (Z)-2-butenedioate (1:1) (salt), m.p. 169°–177° C.,
2. (±)-(1α,2β,4β)-2-(2-methyl- 2-propanamino)-4-(4'-(1-oxo-propoxy)-[1,1'-biphenyl]-4-ylmethyl)-cyclopentan-1-ol hydrochloride, m.p. 195°–215° C.,
3. (±)-(1α,2β,4β)-4-(4'-(2,2-dimethyl-1-oxo-propoxy)-[1,1'-biphenyl]-4-ylmethyl)-2-(2-methyl-2-propanamino)-cyclopentan-1-ol hydrochloride, m.p. 194°–207° C.,
4. (±)-(1α,2β,4α)-4-(4'- acetyloxy -[1,1'-biphenyl]-4-ylmethyl)-2-(2-methyl-2-propanamino)-cyclopentan-1-ol (Z)-2-butenedioate (1:1) (salt), m.p. 172°–186° C.

EXAMPLE VII 1. (±)-(1α,3β,4α)-α-(3-hydroxy-4-(2-methyl-2-propanamino)-cyclopent-1-yl)-4'-methoxy-[1,1'-biphenyl-4-methanol A mixture of (±)-(1α,3α,5α)-4'-methoxy-α-(6-oxabicyclo[3.1.0]hex-3-yl)-[1,1'-biphenyl]-4-methanol (K.4.) (12.1 g), ethanol (120 ml), water (6 ml) and 2-methyl-2-propanamine (80 ml) was heated in an autoclave at 140° C. for 13 h. Solvent was removed in vacuo and moisture was removed from the residue by azeotropic distillation with toluene. The crude product was crystallised from ethanolether to give a mixture of isomeric products (13.45 g). Fractional crystallisation from toluene gave material (5.88 g), which was a pure sample of the faster running isomer on thin layer chromatography. Conversion of this isomer to the maleate salt followed by crystallisations from ethanolacetone gave (±)-(1α,3β,4α)-α-(3-hydroxy-4-(2-methyl-2-propanamino)-cyclopent-1-yl)-4'-methoxy-[1,1'-biphenyl]-4-methanol (Z)-2-butenedioate (1:1) (salt), ISOMER A, (4.55 g), m.p. 195°–200° C.

2. The remaining mother liquor material (free base), which was rich in the slower running isomer on thin layer chromatography (8.0 g), was purified by conversion to the fumarate salt, followed by fractional crystallisation, giving fairly pure material (4.9 g). This material was reconverted to the maleate salt to give (±)-(1α,3β,-4α)-α-(3-hydroxy-4-(2-methyl-2-propanamino)-cyclopent-1-yl)-4-methoxy-[1,1-biphenyl]-4-methanol (Z)-2-butene-dioate (1:1) (salts), ISOMER B, (4.45 g), m.p. 175°–185 ° C.

EXAMPLE VIII

The following compounds were prepared by similar procedures; the primary amino derivatives were prepared by reduction of the intermediate azidoalcohol with lithium aluminium hydride. In some cases the pair of stereo isomers have not been separated. Isomer A denotes the isomer with the larger $R_f$ on thin layer chromatography.
1. (±)-(1α,3α,4β)-α-(3-amino-4-hydroxycyclopent-1-yl)-[1,1'-biphenyl]-4-methanol (Z)-2-butenedioate (1:1) (salt), ISOMER A, m.p. 162°–171° C.,
2. (±)-(1α,3α,4β)-α-(3-amino-4-hydroxycyclopent-1-yl)-[1,1'-biphenyl]-4-methanol (Z)-2-butenedioate (1:1) (salt), ISOMER B, m.p. 181°–184° C.,
3. (±)-(1α,3β,4α)-α-(3-hydroxy-4-(2-methyl-2-propanamino)-cyclopent-1yl)-[1,1'-biphenyl]-4-methanol (Z)-2-butenedioate (1:1) (salt), MIXTURE OF ISOMERS, m.p. 163°–166° C.,
4. (±)-(1α,3β,4α) 4'-hydroxy-α-(3-hydroxy-4-(2-methyl-2-propanamino)-cyclopent-1-yl)-[1,1'-biphenyl]-4-methanol (E)-2-butenedioate (2:1) (salt), MIXTURE OF ISOMERS, m.p. 272°–276° (Decomp.).
5. (±)-(1α,3β,4α)-4'-chloro-α-(3-hydroxy-4-(2-methyl-2-propanamino)-cyclopent-1-yl)-[1,1'-biphenyl]-4-methanol (Z)-2-butenedioate (1:1) (salt), ISOMER A, m.p. 168°–169° C.,
6. (±)-(1α,3β,4α)-4'-chloro-α-(3-hydroxy-4-(2-methyl-2-propanamino)-cyclopent-1-yl)-[1,1'-biphenyl]-4-methanol (Z)-2-butenedioate (1:1) (salt), ISOMER B, m.p. 220°–223° C.,
7. (±)-(1α,3α,4β)-α-(3-hydroxy-4-(2-methyl-2-propanamino)-cyclopent1-yl)-[1,1'-biphenyl]-4- methanol (E)-2-butenedioate (2:1) (salt), ISOMER A, m.p. 246°–249° C., 8. (±)-(1α,3β,4α)-α-(3-amino-4-hydroxycyclopent-1-yl)-[1,1'-biphenyl]-4-methanol (Z)-2-butenedioate (1:1) (salt), ISOMER A, m.p. 185°–187° C., 9. (±)-(1α,3β,4α)-α-(3-amino-4-hydroxycyclopent-1-yl)-[1,1'-bipheny]-4-methanol (Z)-2-butenedioate (1:1) (salt), ISOMER B, m.p. 178°–182 ° C., 10. (±)-(1α,3α,4β)-α-(3-hydroxy-4-(2-methyl-2-propanamino)-cyclopent-1-yl)-4'-methoxy-[1,1'-biphenyl]-4-methanol (Z)-2-butenedioate (1:1) (salt), ISOMER A, m.p. 137°–141° C., 11. (±)-(1α,3α,4β)-α-(3-hydroxy-4-(2-methyl-2-propanamino)-cyclopent-1-yl)-4'-methoxy-[1,1'-biphenyl]-4-methanol (E)-2-butenedioate (2:1) (salt), ISOMER B, m.p. 218°–223° C., 12. (±)-(1α,3α,4β)-4'-hydroxy-α-(3-hydroxy-4-(2 methyl-2-propanamino)-cyclopent-1-yl)-[1,1'-biphenyl]-4-methanol (E)-2-butenedioate (2:1) (salt), MIXTURE OF ISOMERS, m.p. 275°–280° C., 13. (±)-(1α,3α,4β)-4'-chloro-α-(3-hydroxy-4-(2-methyl-2-propanamino)-cyclopent-1-yl)-[1,1'-biphenyl]-4-methanol (Z)-2-butenedioate (1:1) (salt), ISOMER A, m.p. 185°–187° C., 14. (±)-(1α,3α,4β)-4'-chloro-α-(3-hydroxy-4-(2-methyl-2-propanamino)-cyclopent-1-yl)-[1,1'-biphenyl]-4-methanol (Z)-2-butenedioate (1:1) (salt), ISOMER B, (contains 10% ISOMER A), m.p. 174°–178° C., 15. (±)-(1α,3α,4β)-α-(3-hydroxy-4-(2-methyl-2-propanamino)-cyclopent-1-yl)-4-phenoxy-benzenemethanol (Z)-2-butenedioate (1:1) (salt), ISOMER A, m.p. 188°–191° C., 16. (±)-(1α,3α,4β)-α-(3-hydroxy-4-(2-methyl-2-propanamino)-cyclopent-1-yl)-4-phenoxy-benzenemethanol (E)-2-butenedioate (2:1) (salt), ISOMER B, m.p. 205°–216° C., 17. (±)-(1α,3β,4α)-α-(3-hydroxy-4-(2-methyl-propanamino)-cyclopent-1-yl)-4 phenoxy-benzenemethanol (Z)-2-butenedioate (1:1) (salt), ISOMER A, m.p. 137°–138° C., 18. (±)-(1α,3β,4α)-α-(3-hydroxy-4-(2-methyl-2-propanamino)-cyclopent-1-yl)-4-phenoxy-benzenemethanol (E)-2-butenedioate (2:1) (salt), ISOMER B, m.p. 206°–212° C., 19. (±)-(1α,3α,4β )-1-(3-amino-4-hydroxycyclopent-1-yl)-1-([1,1'-biphenyl]-4-yl)-1-propanol (Z)-2-butenedioate (1:1) (salt), ISOMER A, m.p. 167°–169° C., 20. (±)-(1α,3α,4β )-1-(3-amino-4-hydroxycyclopent-1-yl)-1-([1,1'-biphenyl]-4-yl)-1-propanol (Z)-2-butenedioate (1:1) (salt), ISOMER B, m.p. 188°–191° C., 21. (±)-(1α,3β,4α)-1-([1,1'-biphenyl]-4-yl)-1-(3-hydroxy-4-(2-methyl-2-propanamino)-cyclopent-1-yl)-1-propanol (Z)-2-butenedioate (1:1) (salt), ISOMER A, m.p. 179°–183° C., 22. (±)-(1α,3β,4α)-1-([1,1'-biphenyl]-4-yl)-1-(3-hydroxy-4-(2-methyl-2-propanamino)-cyclopent-1-yl)-1-propanol (Z)-2-butenedioate (1:1) (salt), ISOMER B, m.p. 129°–140° C., 23. (±)-(1α,3α,4α)-1-(4'-chloro-[1,1'-biphenyl]-4-yl)-1-(3-hydroxy-4-(2-methyl-2-propanamino)-cyclopent-1-yl)-1-propanol (Z)-2-butenedioate (1:1) (salt), ISOMER A, m.p. 150°–157° C., 24. (±)-(1α,3β,4α)-1-(4'-chloro-[1,1'-biphenyl]-4-yl)-1-(3-hydroxy-4-(2-methyl-2-propanamino)-cyclopent-1-yl)-1-propanol (Z)-2-butenedioate (1:1) (salt), ISOMER B, m.p. 163°–176° C., 25. (±)-(1α,3α,4β)-1-([1,1'-biphenyl]-4-yl)-1-(3-hydroxy-4-(2-methyl-2-propanamino)-cyclopent-1-yl)-1-propanol (Z)-2-butenedioate (1:1) (salt), ISOMER A, m.p. 129°–140° C., 26. (±)-(1α,3α,4β)-1-(1,1'-biphenyl-4-yl)-1-(3-hydroxy-4-(2-methyl-2-propanamino)-cyclopent-1-yl)-1-propanol (Z)-2-butenedioate (1:1) (salt), ISOMER B, m.p. 190°–194° C., 27. (±)-(1α,3α,4β)-1-(4'-chloro-[1,1'-biphenyl]-4-yl)-1-(3-hydroxy-4-(2-methyl-2-propanamino)-cyclopent-1-yl)-1-propanol (Z)-2-butenedioate (1:1) (salt), ISOMER A, m.p. 159°–178° C., 28. (±)-(1α,3α,4β )-1-(4'-chloro-[1,1'-biphenyl]-4-yl)-1-(3-hydroxy-4-(2-methyl-2-propanamino)-cyclopent-1-yl)-1-propanol (Z)-2-butenedioate (1:1) (salt), ISOMER B, m.p. 153°–182° C.

EXAMPLE IX

Preparation of amino-ethers (a)

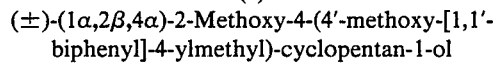
(±)-(1α,2β,4α)-2-Methoxy-4-(4'-methoxy-[1,1'-biphenyl]-4-ylmethyl)-cyclopentan-1-ol Boron trifluoride etherate (8 ml) was added, with stirring, to a cooled suspension of (±)-(1α,3β,5α)-3-(4'-methoxy-[1,1'-biphenyl]-4-ylmethyl)-6-oxabicyclo[3.1.0]hexane (8 g) in methanol (70 ml) and the mixture was stirred at room temperature. After 90 min., the mixture was poured into water and the resultant precipitate was filtered off and dissolved in methylene dichloride. The solution was washed twice with water, once with brine, dried (MgSO$_4$) and the solvent was removed in vacuo. Chromatography of the crude product on silica gel and crystallisation of the material eluted with toluene-ethyl acetate (4:1) from methylene dichloride-ether gave (±)-(1α,2β,4α)-2-methoxy-4 (4'-methoxy-1,1'-biphenyl-4-yl-methyl)-cyclopentan-1-ol (6.6 g) as a white solid, m.p. 97°-98° C. The following compound was made in a similar manner: (±)-(1α,2β,4β)-2-methoxy-4-(4'-methoxy-[1,1'-diphenyl]-4-ylmethyl)-cyclopentan-1-ol, m.p. 72°–74° C., from (±)-(1α,3α,5α)-3-(4'-methoxy-[1,1'-biphenyl]-4-ylmethyl)-6-oxabicyclo[3.1.0]hexane.

(b)

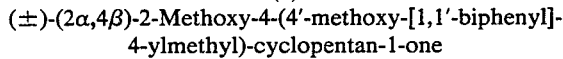
(±)-(2α,4β)-2-Methoxy-4-(4'-methoxy-[1,1'-biphenyl]-4-ylmethyl)-cyclopentan-1-one Jones reagent (12 ml) was added, with stirring, to a cooled solution of (±)-(1α,2β,4α)-2-methoxy-4-(4'-methoxy-[1,1'-biphenyl]-4-ylmethyl) cyclopentan-1-ol (6.6 g) in acetone (70 ml) and the mixture was stirred at room temperature. After 20 min., the reaction mixture was poured into water and the resultant precipitate was filtered off and dissolved in methylene dichloride. The methylene dichloride solution was washed twice with water, once with brine, dried (Mg$_2$SO$_4$) and the solvent was evaporated in vacuo. Successive crystallisations from ether-light petroleum gave (±)-(2α,4β)-2-methoxy-4-(4'-methoxy-[1,1'-biphenyl]-4-ylmethyl)-cyclopentan-1-one (3.9 g) as a white solid, m.p. 81°–82° C. The following compound was made in a similar manner: (±)-(2α,4α)-2-methoxy-4-(4'-methoxy-[1,1'-biphenyl]-4-ylmethyl)-cyclopentan-1-one, m.p. 114°–116° C., from (±)-(1α,2β,4β)-2-methoxy-4-(4'-methoxy-[1,1'-biphenyl]-4-ylmethyl)-cyclopentan-1-ol.

(c) (±)-(1α, 2α,4β)-2-Butanamino-4-(4'-methoxy-[1,1'-biphenyl]-4-ylmethyl)-cyclopentan-1-ol methyl ether hydrochloride N-butylamine (30 ml) was added to a solution of (±)-(2α,4β)-2-methoxy-4-(4'-methoxy-[1,1'-biphenyl]-4-ylmethyl)-cyclopentan-1-one (2.5 g) in ethanol (20 ml) and the solution was stirred at room temperature for 90 min. A small amount of molecular sieve was added and, after 20 min. of stirring, sodium borohydride (800 mg) was added. After a further 20 min. the molecular sieve was filtered off, the filtrate was poured into water and the mixture was extracted with methylene dichloride. The extract was washed twice with water, once with brine, dried (Mg₂SO₄), and the solvent was removed in vacuo to give crude product, which was dissolved in a mixture of chloroform, ethanol and ammonia (300:10:1) and chromatographed on silica gel. Elution with this solvent mixture gave material which was dissolved in methylene dichloride and converted to the hydrochloride by the passage of HCl gas. Two crystallisations from ethanol-ether gave (±)-(1α,2α,4β)-2-butanamino-4-(4'-methoxy-[1,1'-biphenyl]-4-ylmethyl)-cyclopentan-1 ol methyl ether hydrochloride, (1.7 g) as a white solid, m.p. 183°–186° C.

The following compound was obtained in a similar manner: (±)-(1α,2α,4α)-2-butanamino-4-(4'-methoxy-[1,1'-biphenyl]-4-ylmethyl)-cyclopentan-1-ol methyl ether hydrochloride, m.p. 135°–138° C. from (±)-(2α,4α)-2-methoxy-4-(4'-methoxy-[1,1'-biphenyl]-4 ylmethyl)-cyclopentan-1 one.

EXAMPLE X (±)-(1α,2β,4α)-4-([1,1'-biphenyl]-4-ylmethyl)-2-(2-methyl-2-propanamino)-cyclopentan-1-ol 1-acetate hydrochloride Acetic anhydride (2 ml) was added to a solution of (±)-(1α,2β,4α)-4 ([1,1'-biphenyl]-4-ylmethyl)-2-methyl-2-propanamino)-cyclopentan-1-ol (2 g) in acetic acid (5 ml) and the solution was stirred at room temperature for 20 h. A further quantity of acetic anhydride (2 ml) was added and the solution was heated on a water-bath at 95° C. for 3 h. The reaction mixture was poured into water and the product was extracted with methylene dichloride. The extract was washed with sodium hydroxide solution, with water and with brine, dried (MgSO₄), and the solvent was removed in vacuo. The crude product (3.5 g) was dissolved in methylene dichloride and chromatographed on silica gel (50 g). Elution with dichloromethane-ethanol-ammonia (100:10:1) gave material, which was dissolved in methylene dichloride and converted to the hydrochloride. Two recrystallisations from ethanol-ether gave (±)-(1α,2β,4α)-4-([1,1'-biphenyl])-4-ylmethyl)-2-(2-methyl-2-propanamino)-cyclopentan-1-ol 1-acetate hydrochloride as a white solid (1.65 g), m.p. 155°–171° C.

EXAMPLE XI (±)-(1α,2β,4α)-4-([-1,1'-biphenyl]-4-ylmethyl)-2-(2-methyl-2-propanamino)-cyclopentan-1-ol, 1-(2,2-dimethylpropanoate)(Z)-2-butenedioate (1:1) (salt)

A solution of (±)-(1α,2β,4α)-4-([1,1'-biphenyl])-4-ylmethyl-2-(2-methyl-2-propanamino)-cyclopentan-1-ol (2 g) in pivalic acid (2 ml) and pivalic anhydride (4 ml) was heated on a steam bath for 1 h. Extraction and chromatography as described above gave the ester as the free base (2.1 g), which was dissolved in ethanol. Addition of maleic acid (883 mg) gave the crude salt, which was recrystallised twice from ethanol-ether to give (±)-(1α,2β,4α)-4-([1,1'-biphenyl]-4-ylmethyl)-2-(2-methyl-2-propanamion)-cyclopentan-1-ol, 1-(2,2-dimethyl-propanoate)-(Z)-2-butenedioate (1:1) (salt) as a white solid (2.8 g), m.p. 135°–139° C.

EXAMPLE XII

Resolution of (±)-(1α,2β,4β)-4-(4'-methoxy-[1,1'-biphyenyl]-4-ylmethyl)-2 (2 methyl-2-propanamino)-cyclopentan-1-ol (±)-(1α,2β,4β)-4-(4'-methoxy-[1,1'-biphenyl]-4-ylmethyl)-2-(2-methyl-2-propanamino)-cyclopentan-1-ol (7.3 g) was treated with d-10-camphorsulphonic acid (5.16 g) in ethanol and the diastereo-isomeric salts were subjected to repeated fractional crystallisation from ethanol-ether. Further enrichment was achieved by conversion to the hydrochloride salts, and utilising the lower solubility of the salt of the racemic mixture relative to those of the enantiomers. Optical purities were determined by p.m.r., using optical shift reagents and the enantiomers were assigned on the basis of the sign of the specific rotations of the free bases.

(−)-(1α,2β,4β)-4-(4'-methoxy-[1,1'-biphenyl]-4-ylmethyl)-2-(2-methyl-2-propanamino)-cyclopentan-1-ol hydrochloride; m.p. 248°–258° C.; $[\alpha]_D + 30.7°$ (1.08% in CHCl₃); Free base $-[\alpha]_D - 23.3°$ (1.0% in CHCl₃), optical purity 100%.

(±)-(1α,2β,4β)-4-(4'-methoxy-[1,1'-biphenyl]-4-ylmethyl)-2-(2-methyl-2-propanamino)-cyclopentan-1-ol hydrochloride; m.p. 247°–255° C.; $[\alpha]_D - 30.6°$ (0.96% in CHCl₃); Free base $[\alpha]_D + 18.6°$ (0.94% in CHCl₃), optical purity 94%.

Similarly, resolution of (±)-(1α,2β,4α)-4-(4-methoxy-[1,1'-biphenyl]-4-ylmethyl)-2-(2-methyl-2-propanamino)-cyclopentan-1-ol with d-10-camphorsulphonic acid gave the following:

(−)-(1α,2β,4α)-4-(4-methoxy-[1,1'-biphenyl]-4-ylmethyl)-2-(2-methyl-2-propanamino)-cyclopentan-1-ol hydrochloride; m.p. 238°–245°; $[\alpha]_D + 6.1°$ (1.19% in CHCl₃); Free base $[\alpha]_D - 49°$ (0.86% in CHCl₃).

(±)-(1α,2β,4α)-4-(4-methoxy-[1,1'-biphenyl]-4-ylmethyl)-2-(2-methyl-2-propanamino)-cyclopentan-1-ol hydrochloride; m.p. 218°–241° C.; $[\alpha]_D - 5.1°$ (1.16% in CHCl₃); Free base $[\alpha]_D + 33.7°$ (1.17% in CHCl₃).

EXAMPLE XIII (a)

(±)-(2α,4α)-4-([1,1'-biphenyl]-4-ylmethyl)-2-(2-methyl-2-propanamino)-cyclopentan-1-one Kiliani reagent (15 ml) was added, with stirring, to a solution of (±)-(1α,2β,4α)-4-[(1,1'-biphenyl)-4-ylmethyl]-2-(2-methyl-2-propanamino)-cyclopentan-1-ol (3 g) in acetic acid (20 ml), keeping the temperature below 20° C. The mixture was stirred for 24 h., then it was poured into water and the resultant precipitate was filtered off and dissolved in methylene dichloride. The resulting solution was washed once with dilute caustic solution, once with water, and finally with brine. The solution was dried (MgSO₄) and the solvent was evaporated in vacuo. Chromatography of the crude product on silica gel gave (±)-(2α,4α)-4-([1,1'-biphenyl]-4-ylmethyl)-2-(2-methyl 2-propanamino)-cyclopentan-1-one as a brown gum (2.1 g).

(b)
(±)-(1α,2α,4α)-4-([1,1'-biphenyl]-4-ylmethyl)-2-(2-methyl-2-propanamino)-cyclopentan-1-ol hydrochloride Sodium borohydride (0.8 g) was added, portion-wise, to a solution of (±)-(2α,4α)-4-([1,1'-biphenyl]-4-ylmethyl)-2-(2-methyl-2-propanamino)-cyclopentan-1-one (3 g) in ethanol (25 ml) and the mixture was stirred at room temperature for 1 hour. The reaction mixture was poured into water and extracted with methylene dichloride. The methylene dichloride layer was washed once with water and once with brine, dried (Mg SO₄) and the solvent was removed in vacuo. Chromatography of the crude product on silica gel, followed by the bubbling of HCl gas into a cooled methylene dichloride solution of the desired fractions gave the crude hydrochloride, which was recrystallised from ethanol-ether to give (±)-(1α,2α,4α)-4-[1,1'-biphenyl]-4-ylmethyl)-2-(2-methyl-2-propanamino)-cyclopentan-1-ol hydrochloride (1.6 g) as a white solid, m.p. 249°–254° C.

EXAMPLE XIV (±)-(1α,2α,4α)-2-Amino-4-([1,1'-biphenyl]-4-ylmethyl)-cyclopentan-1-ol hydrochloride Benzoyl chloride (3.5 ml) and sodium hydroxide solution (15 ml; 4N) were added to a cooled solution of (±)-(1α,2β,4β)-2-amino-4-[(1,1'-biphenyl)-4-ylmethyl]-cyclopentan-1-ol hydrochloride (3.8 g) in water (100 ml) and the mixture was stirred at room temperature for 90 min. to give an almost colourless solid. The mixture was cooled in an ice-bath and the solid was filtered off and dissolved in methylene dichloride. The methylene dichloride solution was washed twice with water. once with brine, then dried (Mg SO₄) and the solvent was evaporated in vacuo. Crystallisation of the residue from methylene dichloride-ether gave (±)-(1α,2β,4β)-2-benzamido-4-([1,1'-biphenyl]-4-ylmethyl)-cyclopentan-1-ol (3.7 g) as a white solid, m.p. 180°–183° C.

This material (3.2 g) was added to ice-cold thionyl chloride (10 ml) and the mixture was stirred at 30° C. for 2 h. The mixture was poured into iced water, then heated under reflux for 30 min. The mixture was cooled, poured into water, and the solid was filtered off. The solid was heated at reflux temperature with 5N hydrochloric acid (40 ml) for 8 hours, then the mixture was cooled, basified and filtered and the resultant solid was dissolved in methylene dichloride. The methylene dichloride solution was washed once with water, once with brine, dried (Mg SO₄) and the solvent was removed in vacuo. HCl gas was bubbled into a cooled, methylene dichloride solution of the product, and the salt was crystallised from methanol-ether. The product was dissolved in methanol, treated with charcoal and finally crystallised from methanol-ether to give (±)-(1α,2α,4α)-2-amino-4-([1,1'-biphenyl]-4 ylmethyl)-cyclopentan-1-ol hydrochloride (1.65 g) as a white solid, m.p. 259°–261° C.

EXAMPLE XV (±)-(1α,2β,5β)-5-([1,1'-biphenyl]-4-ylmethyl)-2-(2-methyl-2-propanamino)-cyclohexan-1-ol and
(±)-(1α,2β,4α)-4-([1,1'-biphenyl]-4-ylmethyl)-2-(2-methyl-2-propanamino)-cyclohexan-1-ol A solution of 3-([1,1'-biphenyl]-4-ylmethyl)-7-oxabicyclo[4.1.0]heptane (4.5 g) (1:1 cis:trans) in ethanol (30 ml), 2-methyl-2-propanamine (40 ml), and water (2.5 ml) was heated in an autoclave at 140° C. for 14 h. The solvents were removed in vacuo and the crude product (6 g) was chromatographed on silica gel, elution with chloroform-ethanol-ammonia (100:10:1) giving pure samples of the two main products; 2.2 g of the fast spot (TLC) and 2.0 g of the slow isomer. The isomeric assignment was established by 13C nmr and each component was converted to the hydrochloride salt. Crystallisation from ethanol-ether gave (±)-(1α,2β,5β)-5-([1,1'-biphenyl]-4-ylmethyl)-2-(2-methyl-2 propanamino)-cyclohexan-1-ol hydrochloride, m.p. 216°–219° C., fast spot on thin layer chromatography, and (±)-(1α,2β,4α)-4-([1,1'-biphenyl]-4-ylmethyl)-2-(2-methyl-2-propanamino)-cyclohexan-1-ol hydrochloride, m.p. 209°–220° C., slow spot on thin layer chromatography.

The latter compound was also converted into the methanesulphonate salt: m.p. 148°–151° C.

EXAMPLE XVI

Similar treatment(as disclosed in the previous example) of 3-(4'-methoxy-[1,1'-biphenyl]-4-ylmethyl)-7-oxabicyclo[4.1.0]heptane gave (±)-(1α,2β,5β)-5-(4'-methoxy-[1,1'-biphenyl]-4-ylmethyl)-2-(2-methyl-2-propanamino)-cyclohexan-1-ol hydrochloride, m.p. 226°–230° C. and (±)-(1α,2β,4α)-4-(4'-methoxy-[1,1'-biphenyl]-4-ylmethyl)-2-(2-methyl-2-propanamino)-cyclohexan-1-ol hydrochloride, m.p. 211°–215° C.

Treatment of 3-([1,1'-biphenyl]-4-ylmethyl)-7-oxabicyclo[4.1.0]heptane with methylamine, gave (±)-(1α,2β,5β) ([1,1'-biphenyl]-4-ylmethyl)-2-methanamino-cyclohexan-1-ol hydrochloride, m.p. 229°–240° C. and (±)-(1α,2β,4α)-4-([1,1'-biphenyl]-4-ylmethyl)-2-methanamino-cyclohexan-1-ol hydrochloride, m.p. 214°–219° C. In this case, the isomers were separated by chromatography of their benzamido derivatives.

Opening of the epoxide mixture with sodium azide, chromatographic (HPLC) separation of the isomeric azido-ols, followed by lithium aluminium hydride reductions gave the following primary amino-ols; (±)-(1α,2β,5β)-2-amino-5-([1,1'-biphenyl]-4-ylmethyl)-cyclohexan-1-ol hydrochloride, m.p. 241°–244° C. and (±)-(1α, 2β,4α)-2-amino-4-([1,1'-biphenyl]-4-ylmethyl)-cyclohexanl-ol hydrochloride, m.p. 265° C. (decomposition).

We claim:
1. A compound of the forumula

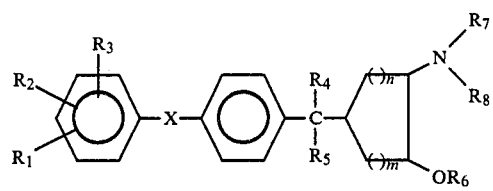

wherein
$R_1$, $R_2$ and $R_3$ is each independently hydrogen alkyl of 1–6 carbon atoms, alkoxy of 1–6 carbon atoms, alkanoyloxy of 1–6 carbon atoms, hydroxy, halogen or optionally alkyl-substituted amino;

$R_4$ is hydrogen, hydroxy or alkyl of 1–6 carbon atoms;

$R_5$ is hydrogen or alkyl of 1–6 carbon atoms;

$R_6$ is hydrogen, acyl derived from an aliphatic carboxylic acid with 1–6 carbon atoms or from phenyl aliphatic carboxylic acid with 7–10 carbon atoms, or alkyl of 1–6 carbon atoms;

each of $R_7$ and $R_8$ is independently hydrogen or alkyl of 1–6 carbon atoms;

X is a direct bond or an oxygen atom, and each of n and m is independently 1 or 2, whereby the sum of n and m is 2 or 3 or a pharmaceutically acceptable salt thereof.

2. Compound according to claim 1 in which X represents a direct bond.

3. Compound according to claim 2 in which $R_4$, $R_5$ and $R_6$ represent hydrogen.

4. Compound according to claim 1, in which the amino substituent to the alicyclic ring is in $\beta$-position and the oxo substituent to the alicyclic ring is in $\alpha$-position.

5. Compound according to claim 7, in which the amino radical is in $\beta$-position and both other substituents to the alicyclic ring are in $\alpha$-position.

6. An anti-arrhythmic composition comprising an anti-arrhydthmic effective amount of a compound of claim 1 and a pharmaceutically acceptable carrier therefor.

7. An anti-arrhythmic composition comprising an anti-arrhythmic effective amount of a compound of claim 2 and a pharmaceutically acceptable carrier therefor.

8. An anti-arrhythmic composition comprising an anti-arrhythmic effective amount of a compound of claim 3 and a pharmaceutically acceptable carrier therefor.

9. An anti-arrhythmic composition comprising an anti-arrhythmic effective amount of a compound of claim 4 and a pharmaceutically acceptable carrier therefor.

10. An anti-arrhythmic composition comprising an anti-arrhythmic effecitve amount of a compound of claim 5 and a pharmaceutically acceptable carrier therefor.

* * * * *